(12) United States Patent
Tsai et al.

(10) Patent No.: US 12,084,725 B2
(45) Date of Patent: Sep. 10, 2024

(54) **OLIGONUCLEOTIDES FOR DETECTING *LACTOBACILLUS* AND METHOD FOR DETECTING *LACTOBACILLUS* BY USING SAME**

(71) Applicant: BENED BIOMEDICAL CO., LTD., Taipei (TW)

(72) Inventors: Ying-Chieh Tsai, Taipei (TW); Chien-Chen Wu, Taipei (TW); Chih-Chieh Hsu, Taipei (TW)

(73) Assignee: BENED BIOMEDICAL CO., LTD., Taipei (TW)

( * ) Notice: Subject to any disclaimer, the term of this patent is extended or adjusted under 35 U.S.C. 154(b) by 742 days.

(21) Appl. No.: 17/147,549

(22) Filed: Jan. 13, 2021

(65) Prior Publication Data
US 2022/0220535 A1    Jul. 14, 2022

(51) Int. Cl.
*C12Q 1/68* (2018.01)
*C12Q 1/6851* (2018.01)
*C12Q 1/689* (2018.01)

(52) U.S. Cl.
CPC ............ *C12Q 1/689* (2013.01); *C12Q 1/6851* (2013.01)

(58) Field of Classification Search
None
See application file for complete search history.

(56) References Cited

PUBLICATIONS

Liu et al. (Gut Pathog 2015, 7:22, p. 2-7) (Year: 2015).*
Mansoor et al. (Accession CP028421; published Apr. 2018) (Year: 2018).*
Lowe et al. (Nucleic Acids Research, 1990, 18(7):1757-1761) (Year: 1990).*

* cited by examiner

*Primary Examiner* — Stephanie K Mummert
(74) *Attorney, Agent, or Firm* — Sughrue Mion, PLLC

(57) ABSTRACT

Provided are compositions and methods for identifying a specific strain of *Lactobacillus plantarum*, e.g., *Lactobacillus plantarum* subsp. *plantarum* PS128 deposited under DSMZ Accession No. DSM 28632.

10 Claims, 3 Drawing Sheets
Specification includes a Sequence Listing.

OLIGONUCLEOTIDES FOR DETECTING *LACTOBACILLUS* AND METHOD FOR DETECTING *LACTOBACILLUS* BY USING SAME

BACKGROUND

1. Technical Field

This disclosure relates to nucleic acids, probes, kits and methods for detection of organisms, including a strain of *Lactobacillus* sp.

2. Description of Related Art

Lactic acid bacteria (hereinafter, referred to as LAB) are bacteria that are capable of converting carbohydrate substrates into organic acids, mostly lactic acid, and producing a wide range of metabolites. LAB has been found to possess many health beneficial effects when administered to animals. For example, LAB is shown effective in helping with gut health, because of their capability in regulating host's gut microbiota, and found effective in preventing or treating abdominal pain, diarrhea, constipation, and bloating.

LAB is also shown to modulate host's mental and physical responses for psychological stress. Stress is one of the factors inducing mood disorders and neurochemical changes in both human and animals, and can lead to stress-induced disorders including anxiety, depression and irritable bowel syndrome. Therefore, stress-induced disorders can be treated by LAB as a supplement, in addition to the conventional psychiatric medicines, as LAB has been shown to have an influence on host gut-brain axis (GBA). For example, *Lactobacillus rhamnosus* is shown to alter functions of the central nerve system in healthy mice through vagus nerve, and the stressed rats supplemented with the probiotic strain *Bifidobacterium infantis* have reversed the behavioral deficits in forced swimming test (FST) and restored basal noradrenaline (NA) level in brain stem.

However, LAB constitutes a heterogeneous group and is found in diverse nutrient-rich habitats associated with plant and animal's matter, as well as in respiratory, gastrointestinal, and genital tracts of humans. Within the Firmicutes phylum, LAB members belong to the order *Lactobacillales* and comprise the following genera: *Aerococcus, Alloiococcus, Carnobacterium, Enterococcus, Lactobacillus, Lactococcus, Leuconostoc, Oenococcus, Pediococcus, Streptococcus, Tetragenococcus, Vagococcus,* and *Weissella*. Among these, *Lactobacillus* is the largest genus of the LAB group, with over 100 species in total. For an instance, from the spontaneously fermented mustard products named "fu-tsai" and "suan-tsai," which are traditionally prepared by the Hakka tribe of Taiwan, 500 LAB isolates were analyzed and identified as 119 representative strains belonging to 5 genera and 18 species, including *Enterococcus* (1 species), *Lactobacillus* (11 species), *Leuconostoc* (3 species), *Pediococcus* (1 species), and *Weissella* (2 species).

Furthermore, the probiotic properties of LAB are strain-specific, as these bacteria adapt to different environments and evolve accordingly. Therefore, it is necessary to be able to identify a specific strain of LAB from others, especially when the LAB strain has been discovered to possess certain health beneficial properties. For example, a LAB strain PS128 has been found to decrease serum corticosterone and alleviate a stress-induced disorder or a psychiatric disorder in a subject as demonstrated in EP Patent No. 2937424B1. The emotional calming effect of PS128 is found to extend to other non-human animals such as dogs (WO 2020/156418 A1). The LAB strain PS128 also claims to treat functional gastrointestinal disorder such as constipation and functional dyspepsia (US10188684B2). The LAB strain PS128 is also shown to prevent or treat a movement disorder such as tic disorders and basal ganglia disorders by modulating dopamine neurotransmission in basal ganglia (WO 2018/014225 A1). Also, the LAB strain PS128 is shown to enhance physical strength and performance in a subject by increasing endurance and reducing muscle fatigue or muscle damage (WO 2020/156417 A1).

Hence, a method to specifically identify and discriminate a LAB strain from others is in need.

SUMMARY

The present disclosure provides a method for detecting a *Lactobacillus* species, *Lactobacillus plantarum* subsp. *plantarum* PS128 (hereinafter referred to as PS128). PS128 is deposited under DSMZ Accession No. DSM 28632. The method involves amplifying a nucleic acid sequence of PS128. The method further involves detecting the amplification product. The present disclosure also encompasses nucleic acids that can be used as primers to amplify a genomic nucleic acid sequence of PS128. In an embodiment, the nucleic acids used as primers hybridize to specific sequences of PS128 under nonarbitrary hybridization conditions. In an embodiment, the nucleic acid sequence of PS128 amplified by the primers is unique to the PS128 strain. The primers can be chemically synthesized oligonucleotides having the sequences 5'-TGTTGG-GATGTTCTCTGCCT-3' (SEQ ID NO: 1) or 5'-ACATT-TACTGCGTTCTGTGC-3' (SEQ ID NO: 2), or the corresponding complementary sequences. For example, the nucleic acid used as a primer has a sequence that contains at least 12, 13, 14, 15, 16, 17, 18 or 19 consecutive nucleotides, or the full length, of the above-identified sequences, as long as they can specifically hybridize to the nucleic acid sequence of PS128 and lead to an amplification product. In an embodiment, the amplification product amplified by the primers of the above-identified sequences is around 900 base pairs (bp), e.g., 890 bp, 895 bp, 900 bp, 905 bp, 910 bp, 915 bp, 920 bp, 925 bp and 930 bp. In another embodiment, the amplification product is 915 base pairs.

In an embodiment, the primers (or probes) can be provided in a detection kit. The kit may also include positive and negative controls for the above species. The positive control can be any sample that contains a target DNA to be amplified, including the bacteria themselves, at an amount over the detection limit. The negative control is a sample that does not contain the target DNA to be amplified.

In one embodiment, the amplification step of the method of the present disclosure is accomplished by polymerase chain reaction (PCR). In some embodiments, the amplification reaction may be selected from the group consisting of polymerase chain reaction (PCR), strand displacement amplification (SDA), nucleic acid sequence based amplification (NASBA), rolling circle amplification (RCA), T7 polymerase mediated amplification, T3 polymerase mediated amplification, and SP6 polymerase mediated amplification.

In one embodiment, the amplification product is detected by gel electrophoresis, mass spectroscopy, or a single stranded DNA detection technique such as fluorescence resonance energy transfer (FRET).

In one aspect, provided are reaction mixtures. In some embodiments, the reaction mixtures comprise: (i) a sample comprising a nucleic acid template; and (ii) one or more oligonucleotide pairs configured to detect the presence or absence of a unique genomic sequence of PS128. In some embodiments, the oligonucleotide pairs detect the unique genomic sequence region of PS128. In some embodiments, the one or more oligonucleotide pairs comprise a forward primer having the sequence of SEQ ID NO: 1, or the complementary sequence of SEQ ID NO: 1, and a reverse primer of SEQ ID NO: 2, or the complementary sequence of SEQ ID NO: 2. In some embodiments, the nucleic acid template comprises genomic DNA. In some embodiments, the reaction mixture further comprises a polymerase and dNTPs.

In another aspect, provided are kits. In some embodiments, the kits comprise an oligonucleotide pair that specifically identify the presence or absence of a unique genomic sequence of PS128. In some embodiments, the one or more oligonucleotide pairs comprise a forward primer having the sequence of SEQ ID NO: 1, or the complementary sequence of SEQ ID NO: 1, and a reverse primer of SEQ ID NO: 2, or the complementary sequence of SEQ ID NO: 2.

Other advantages and features of the present disclosure will become apparent from the following detailed descriptions of this disclosure.

DETAILED DESCRIPTION OF THE EMBODIMENTS

Figure 1:
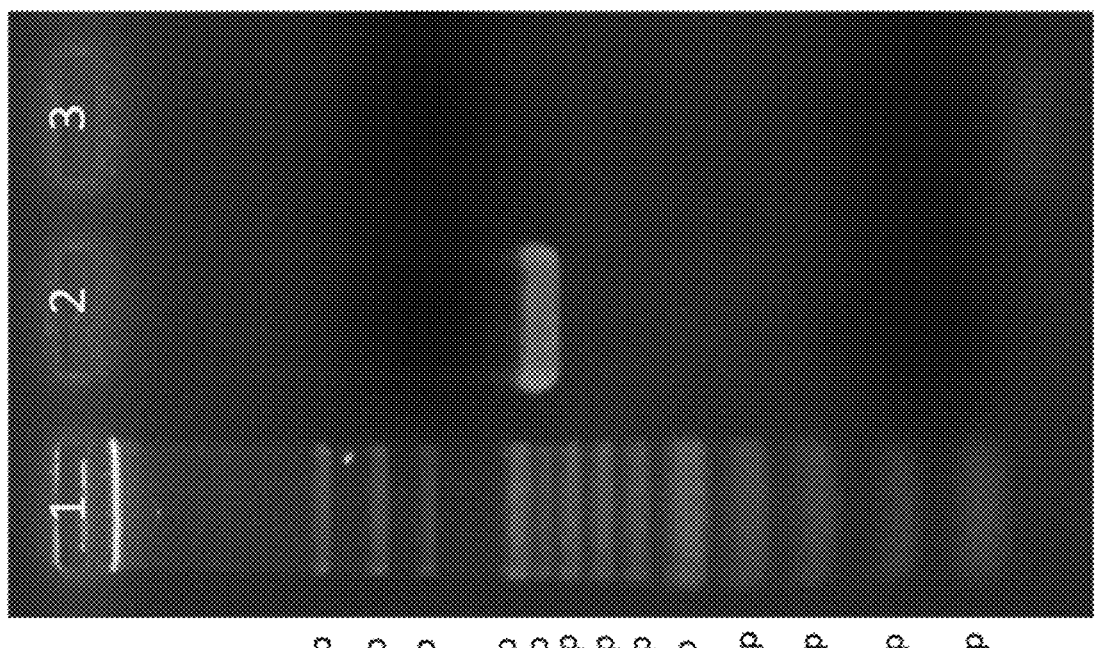
FIG. 1 is a photograph of electrophoresis gel showing the amplification result of PCR using PS128 as the sample with a forward primer having the sequence of SEQ ID NO: 1 and a reverse primer having the sequence of SEQ ID NO: 2 (lane 2). Lane 1 shows the 100 bp ladders for estimating the size of PCR products. Lane 3 is a negative control using *L. plantarum* ATCC 14917$^T$ as the sample.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry and nucleic acid chemistry and hybridization described below are those well-known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (e.g., Green and Sambrook et al., MOLECULAR CLONING: A LABORATORY MANUAL, 4th ed. (2012) Cold Spring Harbor Laboratory Press, Cold Spring Harbor, N.Y. and Ausubel, ed., Current Protocols in Molecular Biology, 1990-2017, John Wiley Interscience), which are provided throughout this document. The nomenclature used herein and the laboratory procedures in analytical chemistry and organic synthesis described below are those well-known and commonly employed in the art. Standard techniques, or modifications thereof, are used for chemical syntheses and chemical analyses.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term "nucleic acid" is used interchangeably with gene, cDNA, mRNA, oligonucleotide, and polynucleotide.

The phrase "nonarbitrary hybridization conditions" refers to conditions under which a probe will hybridize to its target subsequence, typically in a complex mixture of nucleic acid, but to no other sequences. Nonarbitrary conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, the nonarbitrary conditions may be stringent conditions selected to be about 5 to 10° C. lower than the thermal melting point for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times of background, optionally 10 times of background hybridization. Exemplary conditions for stringent hybridization can be as following: 50% formamide, 5× saline-sodium citrate (SSC), and 1% sodium dodecyl sulfate (SDS), incubating at 42° C., or 5×SSC, 1% SDS, incubating at 65° C., with wash in 0.2×SSC, and 0.1% SDS at 65° C.

Nucleic acids that do not hybridize to each other under stringent conditions may still be substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C.

A positive hybridization is at least twice background. Those of ordinary skill will readily recognize that alternative hybridization and wash conditions can be utilized to provide conditions of similar stringency.

The phrase "selectively (or specifically) hybridizes to" refers to the binding, duplexing, or hybridizing of a molecule only to a particular nucleotide sequence under the given hybridization conditions when that sequence is present in a complex mixture (e.g., total cellular or library DNA or RNA).

The amplification of nucleic acids can be effected by the PCR method developed by Seiki et al. (Science, 230, 1350 (1985)). This method comprises preparing two oligonucleotides, one recognizing and hybridizing with the plus strand and the other recognizing and hybridizing with the minus strand at both ends of a specific nucleic sequence region to be detected, causing them to function as primers for the template-dependent nucleotide polymerization reaction against the sample nucleic acid in the single stranded form as a result of heat denaturation, separating the resulting double-stranded nucleic acid into single strands, and again allowing the same reaction to proceed. By repeating this serial procedure, the number of copies of the region between the two primers is increased so that said region can be detected.

The following specific examples are used for illustrating the present disclosure. A person skilled in the art can easily conceive the other advantages and effects of the present disclosure. The present disclosure can also be implemented by different cases enacted or application, and the details of the instructions can also be based on different perspectives and applications in various modifications and changes that do not depart from the spirit of the disclosure.

Many examples have been used to illustrate the present disclosure. The examples below should not be taken as a limit to the scope of this disclosure.

EXAMPLES

Example 1. Identification of *Lactobacillus plantarum* subsp. *plantarum* PS128 by polymerase chain reaction (PCR)

PCR carried out with specific primers designed to amplify the unique genomic sequence region of PS128 was conducted to distinguish the bacteria with high sequence similarity.

The PCR of PS128 was carried out using 20 ng of DNA extracted from PS128, with reagents listed in Table 1 under the condition indicated in Table 2. DNAs extracted from this strain were used as templates. The obtained amplification products were electrophoresed, and the result was shown in FIG. 1, wherein the primers represented by SEQ ID NO: 1 and SEQ ID NO: 2 below were used.

Forward primer:
(SEQ ID NO: 1)
5'-TGTTGGGATGTTCTCTGCCT-3'

Reverse primer:
(SEQ ID NO: 2)
5'-ACATTTACTGCGTTCTGTGC-3'

TABLE 1

Composition of the PCR reaction solution
(25 μL per PCR tube)

| PCR reagents | Volume |
| --- | --- |
| Template DNA (10 ng/μL) | 2.0 μL |
| 10X Ex Taq Buffer* (Mg²⁺ plus) | 2.5 μL |
| dNTP (2.5 mM) | 2.0 μL |
| Forward primer (10 μM) | 2.0 μL |
| Reverse primer (10 μM) | 2.0 μL |
| TaKaRa Ex Taq* (5 U/μL) | 0.2 μL |
| ddH₂O | 14.3 μL |

*Takara Bio U.S.A., Inc.

TABLE 2

| PCR Conditions | | |
| --- | --- | --- |
| Temperature | Time | Cycle |
| 95° C. | 5 min | |
| 95° C. | 30 sec | 30 cycles |
| 59° C. | 30 sec | |
| 72° C. | 60 sec | |
| 72° C. | 10 min | |

As shown in FIG. 1, lane 1 represents DNA ladder (100-3000 bp); lane 2 represents the amplification product with a size of around 900 bp by using PS128 DNA as the DNA template; and lane 3 represents the PCR result of *Lactobacillus plantarum* ATCC 14917$^T$, which is used as the negative control.

Example 2. Specificity of the PCR Method for Detection of PS128

To test the specificity of the PCR method of the present disclosure, primers having sequences of SEQ. ID NOs: 1 and 2 were used to amplify other strains of *Lactobacillus plantarum*.

A total of 7 different strains of *Lactobacillus plantarum* were obtained, as shown in Table 3 below.

TABLE 3

Other tested *Lactobacillus plantarum* strains

| *Lactobacillus plantarum* strains | Source |
| --- | --- |
| 299v | Probi AB, Sweden |
| LP-115 | Dupont, USA |
| 14D | Centro Sperimentale del Latte, Italy |
| $LP_{LDL}$ | OptiBiotix Health, UK |
| TWK-10 | Synbio Tech, Taiwan |
| GL208 | Glac Biotech, Taiwan |
| ATCC 14917$^T$ | Bioresource Collection and Research Center, Taiwan |

Figure 2:
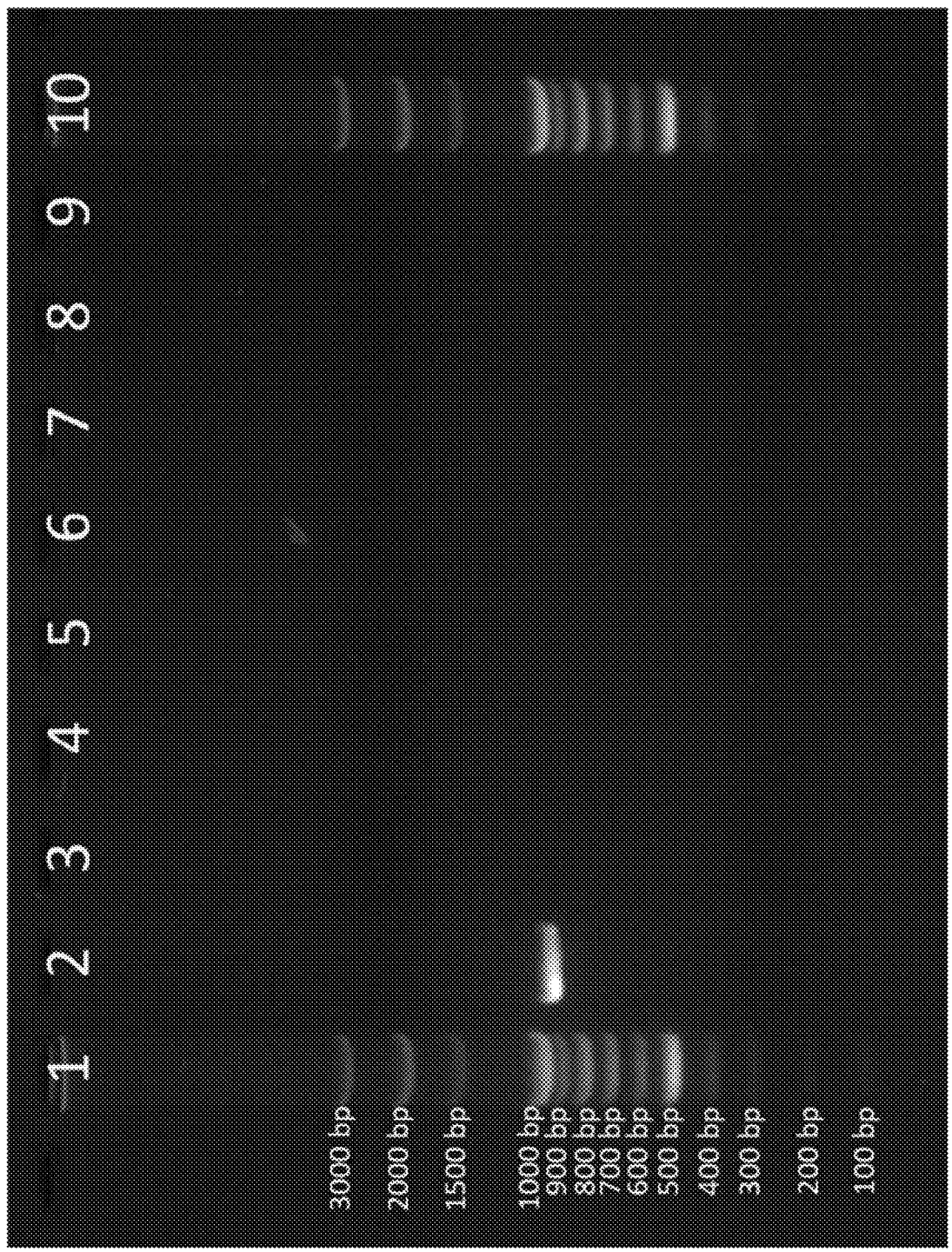
FIG. 2 is a photograph of electrophoresis gel showing the amplification result of PCR using PS128 (lane 2), *L. plantarum* 299v (lane 3), *L. plantarum* LP-115 (lane 4), *L. plantarum* 14D (lane 5), *L. plantarum* LP$_{LDL}$ (lane 6), *L. plantarum* TWK-10 (lane 7), *L. plantarum* GL208 (lane 8), and *L. plantarum* ATCC 14917$^T$ (lane 9) as the samples, respectively, with a forward primer having the sequence of SEQ ID NO: 1 and a reverse primer having the sequence of SEQ ID NO: 2. Lanes 1 and 10 show the 100 bp ladders for estimating the size of PCR products.

The seven different *Lactobacillus plantarum* strains obtained were subjected to amplification with the PCR reagents and conditions shown in Tables 1 and 2 above using the pair of primers having sequences of SEQ ID NOs: 1 and 2, as described in Example 1 above. As shown in FIG. 2, none of these seven strains showed amplification product with size around 900 bp. The result showed that the primers are strain-specific for PS128 identification.

As a comparison, the primer pair reported by Song et al. (Song Y L, Kato N, Liu C X, Matsumiya Y, Kato H, Watanabe K. (2000) "Rapid identification of 11 human intestinal *Lactobacillus* species by multiplex PCR assays using group- and species-specific primers derived from the 16S-23S rRNA intergenic spacer region and its flanking 23S rRNA." FEMS Microbiol. Lett. 187:167-173) with a forward primer having a sequence of 5'-ATTCAT-AGTCTAGTTGGAGGT-3'(SEQ ID NO: 3) and a reverse primer having a sequence of 5'-CCTGAACTGAGAGAAT-TTGA-3'(SEQ ID NO: 4) claims to identify human intestinal species *Lactobacillus plantarum* by PCR.

Figure 3:
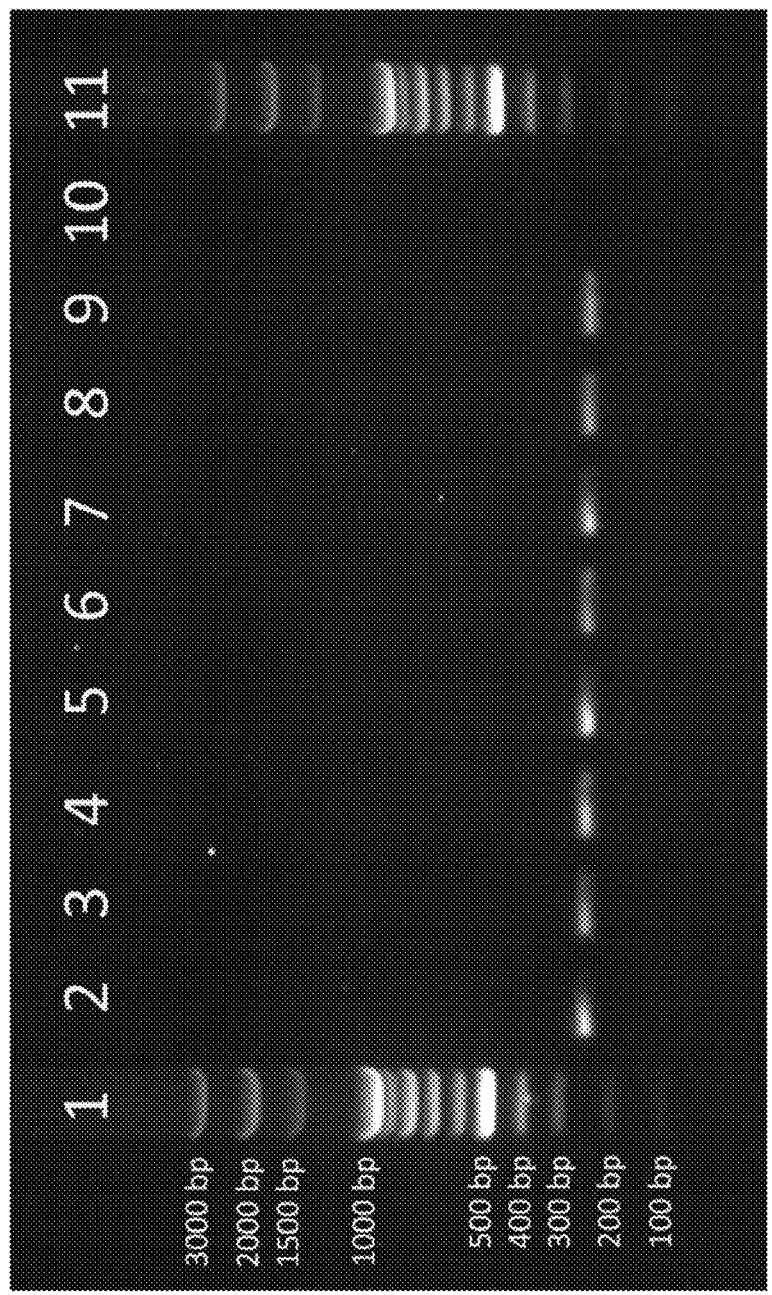
FIG. 3 is a photograph of electrophoresis gel showing the amplification result of PCR using PS128 (lane 2), *L. plantarum* 299v (lane 3), *L. plantarum* LP-115 (lane 4), *L. plantarum* 14D (lane 5), *L. plantarum* LP$_{LDL}$ (lane 6), *L. plantarum* TWK-10 (lane 7), *L. plantarum* GL208 (lane 8) and *L. plantarum* ATCC 14917T (lane 9) as the samples, respectively, and a negative control using *Lactobacillus rhamnosus* GG (lane 10) as the sample with a forward primer having the sequence of SEQ ID NO: 3 and a reverse primer having the sequence of SEQ ID NO: 4. Lanes 1 and 11 show the 100 bp ladders for estimating the size of PCR products. The lanes 2 to 9 all show bands at 248 bp.

The PCR is repeated under the same condition as above with the seven different *Lactobacillus plantarum* strains and PS128, using the primer pair reported by Song et al. The result was shown in FIG. 3. The primer pair reported by Song et al. produced similar bands with a PCR product size of 248 bp for all tested species of *Lactobacillus plantarum* including eight strains in addition to the species *Lactobacillus rhamnosus* bacteria.

While some of the embodiments of the present disclosure have been described in detail in the above, it is, however, possible for those of ordinary skill in the art to make various modifications and changes to the particular embodiments shown without substantially departing from the teaching and advantages of the present disclosure. Such modifications and changes are encompassed in the spirit and scope of the present disclosure as set forth in the appended claims.

What is claimed is:

1. A method for detecting *Lactobacillus plantarum* subsp. *plantarum* PS128, comprising:
   providing a sample comprising a nucleic acid template;
   providing a pair of nucleic acids as primers;
   amplifying a nucleic acid sequence of the *Lactobacillus plantarum* subsp. *plantarum* PS128 with said primers; and
   detecting a product of the amplification,
   wherein said pair of nucleic acids comprises at least 12 consecutive nucleotides of SEQ ID NOs: 1 and 2, respectively,
   wherein said product of the amplification has a size of around 900 base pairs.

2. The method according to claim 1, wherein said pair of nucleic acids comprises at least 15 consecutive nucleotides of SEQ ID NOs: 1 and 2, respectively.

3. The method according to claim 1, wherein said pair of nucleic acids comprises at least 18 consecutive nucleotides of SEQ ID NOs: 1 and 2, respectively.

4. The method according to claim 1, wherein said pair of nucleic acids consists of nucleic acid sequences of SEQ ID NOs: 1 and 2, respectively.

5. The method according to claim 1, wherein said amplification is performed by one selected from the group consisting of polymerase chain reaction (PCR), strand displacement amplification (SDA), nucleic acid sequence based amplification (NASBA), rolling circle amplification (RCA), T7 polymerase mediated amplification, T3 polymerase mediated amplification and SP6 polymerase mediated amplification.

6. The method according to claim 1, wherein said detection is performed by gel electrophoresis, mass spectroscopy, or single stranded DNA detection technique.

7. The method according to claim 6, wherein the single stranded DNA detection technique includes fluorescence resonance energy transfer (FRET).

8. A reaction mixture, comprising:
   (i) a sample comprising a nucleic acid template; and
   (ii) a pair of nucleic acids configured to determine a presence or absence of a genomic sequence of *Lactobacillus plantarum* subsp. *plantarum* PS128,
   wherein the pair of nucleic acids comprises at least 12 consecutive nucleotides of SEQ ID NOs: 1 and 2, respectively.

9. The reaction mixture of claim 8, further comprising a polymerase and dNTPs.

10. A kit comprising a pair of nucleic acids for identifying a presence or absence of a genomic sequence of *Lactobacillus plantarum* subsp. *plantarum* PS128, wherein the pair of nucleic acids comprises at least 12 consecutive nucleotides of SEQ ID NO: 1 and 2, respectively.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 1
tgttgggatg ttctctgcct                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 2
acatttactg cgttctgtgc                                          20

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide, comparison primer

<400> SEQUENCE: 3
attcatagtc tagttggagg t                                        21

<210> SEQ ID NO 4
<211> LENGTH: 20
<212> TYPE: DNA
<213> ORGANISM: Artificial Sequence
<220> FEATURE:
```

-continued

```
<223> OTHER INFORMATION: Synthetic oligonucleotide, comparison primer

<400> SEQUENCE: 4
cctgaactga gagaatttga                                                      20
```